(12) United States Patent
Kuroda et al.

(10) Patent No.: US 11,517,613 B2
(45) Date of Patent: Dec. 6, 2022

(54) LACTASE BULK POWDER AND LACTASE PREPARATION

(71) Applicant: AMANO ENZYME INC., Nagoya (JP)

(72) Inventors: Manabu Kuroda, Kakamigahara (JP); Masayuki Hojo, Kakamigahara (JP)

(73) Assignee: AMANO ENZYME INC., Nagoya (JP)

(*) Notice: Subject to any disclaimer, the term of this patent is extended or adjusted under 35 U.S.C. 154(b) by 189 days.

(21) Appl. No.: 16/620,467

(22) PCT Filed: May 31, 2018

(86) PCT No.: PCT/JP2018/021025
§ 371 (c)(1),
(2) Date: Dec. 6, 2019

(87) PCT Pub. No.: WO2018/225623
PCT Pub. Date: Dec. 13, 2018

(65) Prior Publication Data
US 2021/0145942 A1   May 20, 2021

(30) Foreign Application Priority Data
Jun. 7, 2017 (JP) .............................. JP2017-112848

(51) Int. Cl.
*A61K 38/47* (2006.01)
*A23L 33/125* (2016.01)

(52) U.S. Cl.
CPC ............ *A61K 38/47* (2013.01); *A23L 33/125* (2016.08); *C12Y 302/01108* (2013.01)

(58) Field of Classification Search
None
See application file for complete search history.

(56) References Cited

U.S. PATENT DOCUMENTS

| 5,891,873 | A | 4/1999 | Colaco et al. |
| 5,955,448 | A | 9/1999 | Colaco et al. |
| 6,034,080 | A | 3/2000 | Colaco et al. |
| 6,313,102 | B1 | 11/2001 | Colaco et al. |
| 2006/0008555 | A1 | 1/2006 | Merrill et al. |
| 2009/0238917 | A1 | 9/2009 | Merrill et al. |
| 2012/0189733 | A1 | 7/2012 | Braun |
| 2012/0230973 | A1 | 9/2012 | Goto et al. |
| 2017/0215449 | A1 * | 8/2017 | Nagahata ............... A23C 9/152 |

FOREIGN PATENT DOCUMENTS

| EP | 1208848 A1 * | 5/2002 | ............ A61K 31/70 |
| EP | 1208848 A1 | 5/2002 | |
| EP | 2 481 417 | 8/2012 | |
| JP | H10-505591 A | 2/1998 | |
| JP | 2002-187854 A | 7/2002 | |
| JP | 2002187854 A * | 7/2002 | ............... A61P 1/14 |
| JP | 2016-129525 A1 | 7/2016 | |
| WO | WO 2011/037058 A1 | 3/2011 | |
| WO | WO 2016/060224 A1 | 4/2016 | |
| WO | WO-2016060224 A1 * | 4/2016 | ............... C12N 9/96 |

OTHER PUBLICATIONS

EngMT—Bruce, R.D. et al. Stable lactase composition. Japanese Patent Application Publication No. JP2002187854A; Pub. Date: Jul. 5, 2002, pp. 1-18; specif. pp. 2, 7, 11.*
EngMT. Nagahata, N. & Horiguchi, H. Lactase solution and milk using same. International Patent Application No. WO 2016/060224A1. Date of Pub.: Apr. 21, 2016. pp. 1-11.*
Extended European Search Report dated Nov. 19, 2020 in European Application No. 18813894.5.
International Search Report, dated Aug. 28, 2018, for International Patent Application No. PCT/JP2018/021025.
Protein, nucleic acid and enzyme, vol. 41, No. 6 (1996) pp. 810-816.

* cited by examiner

*Primary Examiner* — Olivia M. Wise
*Assistant Examiner* — Sharon M. Papciak
(74) *Attorney, Agent, or Firm* — Knobbe, Martens, Olson & Bear LLP

(57) ABSTRACT

A lactase bulk powder and a lactase preparation both have improved storage stability. The stability of a lactase bulk powder is improved by regulating the acceptable amount of glucose and/or galactose, generated during manufacturing the lactase bulk powder, within a preset range. The lactase bulk powder includes lactase, galactose and/or glucose. The total amount of galactose and glucose is more than 0 μmol and not more than 50 μmol per 100,000 U of lactase. The lactase preparation has the lactase bulk powder as an active ingredient.

10 Claims, 2 Drawing Sheets

LACTASE BULK POWDER AND LACTASE PREPARATION

PRIORITY AND CROSS REFERENCE TO RELATED APPLICATIONS

This application is the U.S. National Stage Application under 35 U.S.C. § 371 of International Application No. PCT/JP2018/021025, filed May 31, 2018, designating the U.S. and published as WO 2018/225623 A1 on Dec. 13, 2018, which claims the benefit of Japanese Patent Application No. JP 2017-112848, filed Jun. 7, 2017. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present invention relates to a lactase bulk powder and a lactase preparation. More specifically, the present invention relates to a lactase bulk powder and a lactase preparation, each of which can be produced industrially and has high storage stability.

BACKGROUND ART

Lactase is an enzyme capable of hydrolyzing lactose into glucose and galactose, and is also known as "β-galactosidase".

Lactose is contained in a dairy product such as milk. When a dairy product is ingested, lactose is decomposed in vivo with lactase which occurs in the small intestine in most humans, and is then absorbed through the small intestine. However, in some humans, a sufficient amount of lactase is not present in the small intestine. Accordingly, when a dairy product is ingested, the proper absorption in the small intestine does not occur, resulting in the development of symptoms such as dyspepsia, diarrhea and abdominal fullness. This clinical condition is called as "lactase intolerance".

It is well known to take a lactase preparation for the purpose of suppressing the symptoms of lactase intolerance. Therefore, lactase preparations have been manufactured and sold in many countries. On the other hand, it is known that the effect of lactase is decreased or eliminated when lactase is taken before the ingestion of a dairy product. Patent Document 1 discloses a technique for decomposing lactose in vivo while avoiding the deactivation of lactase even when a lactase preparation is taken before the ingestion of a lactose-containing food or beverage, by use of a lactase preparation containing lactase and at least one antacid selected from trisodium citrate, potassium sodium tartrate, calcium carbonate, sodium carbonate and dibasic calcium phosphate.

In general, in the production of a biological preparation such as an enzyme drug, it is recommended to dry an unstable biologically active substance together with an easily vitrescible excipient so as to encapsulate the unstable biologically active substance in a water-soluble glass for the purpose of stabilizing the unstable biological substance, as disclosed in Non-Patent Document 1. In Non-Patent Document 1, it is disclosed that a carbohydrate is important as an excipient, and glycerol, ribose, xylose, sorbitol, mannitol, fructose, glucose, galactose, sucrose, maltose, lactose, trehalose, maltotricose and raffinose are mentioned as examples of an easily vitrescible carbohydrate.

In Patent Document 2, on the other hand, it is noted that Maillard reaction occurs during and after the drying of a biological substance which is carried out in the presence of a carbohydrate excipient capable of stabilizing an enzyme by addition of an amorphous or glass-like solid matrix. In this document, it is reported that the degree of coloration due to the Maillard reaction may correlate with the degree of deterioration of an enzymatic activity. Then, for the purpose of preventing the occurrence of Maillard reaction by the carbohydrate excipient and prolonging the life of the dried biological substance, a method is disclosed, in which the biological substance is dried in the presence of the carbohydrate excipient in an effective amount for the stabilization of the dried biological substance and also in the presence of a Maillard reaction inhibitor in an effective amount for the substantial prevention of the occurrence of the Maillard reaction. As a specific example, it was demonstrated that the activity of an alkaline phosphatase was improved by drying the enzyme in the presence of glucose, which serves as a carbohydrate excipient, while adding lysine, which serves as a Maillard reaction inhibitor, to the enzyme.

In Patent Document 3, it is mentioned that, in the cooking/preparation of a food using an enzyme, water contained in a starting component of the food can cause Maillard brownish discoloration. In addition, it is disclosed that the degree of the Maillard brownish discoloration is reduced with the reduction in the amount of water and, therefore, means for controlling the Maillard brownish discoloration is to reduce the amount of water in the starting component of the food. On the other hand, it is noted that, in the cooking/preparation of a food, the drying of the food through the removal of water, which is means for controlling the Maillard brownish discoloration, may cause another problem. Then, as the means for solving the problem, a method for producing a food (cheese) is disclosed, in which a water-based mixture prepared by adding an oxidoreductase enzyme in an effective amount for the prevention of the occurrence of excess brownish discoloration is formed in a starting component (e.g., whole milk or defatted milk) of the food and then the product is dried.

PRIOR ART DOCUMENTS

Patent Documents

Patent Document 1: International Publication No. 2011/037058
Patent Document 2: Japanese Translation of PCT International Application Publication No. 10-505591
Patent Document 3: Japanese Patent Application Laid-open No. 2016-129525

Non-Patent Document

Non-Patent Document 1: Protein, nucleic acid and enzyme, Vol. 41, No. 6 (1996) pp. 810-816

SUMMARY

Patent Document 1 addresses the problem of the deterioration of the activity of a lactase preparation in vivo upon the intake of the lactase preparation, but does not disclose about the problem associated with the storage stability of the lactase preparation itself. Non-Patent Document 1 describes that an excipient such as glucose and galactose is needed for the production of a biological preparation such as an enzyme drug from the viewpoint of storage stability. Patent Document 2 has an object of preventing the occurrence of Maillard reaction, which is assumed to correlate with the degree of the deterioration of an enzymatic activity, as another problem which may be caused by a carbohydrate excipient. However, the means for solving the problem according to Patent Document 2 is predicated on the drying in the presence of a carbohydrate excipient such as glucose, as in the case of Patent Document 1. Patent Document 3 discloses that a causal factor of Maillard brownish discoloration is the presence of water and, therefore, Maillard brownish discoloration can be prevented by removing water.

However, any one of the documents does not suggest a causal factor other than a carbohydrate excipient such as glucose as a factor affecting the stability of an enzyme during storage. In addition, there is found no suggestion about a causal factor other than a carbohydrate excipient such as glucose or water as a factor affecting Maillard reaction which is disclosed as correlating with the degree of deterioration in an enzymatic activity.

An enzyme including lactase which is produced industrially has been conventionally produced utilizing a microbial fermentation activity, from the viewpoint of production efficiency and production cost. Examples of the method that can be employed for the production of an enzyme using a microorganism include a solid culture method and a liquid culture method. In these culture methods, a culture medium containing a sugar has been used.

A sugar hydrolase produced by microbial fermentation, such as lactase and amylase, can decompose a sugar contained in a culture medium. Thus, glucose or galactose is contained unavoidably in industrially produced lactase as a decomposition product of a sugar contained in a culture medium or a sugar added to a culture medium during the process. It is considered that the amount of glucose or galactose that is produced unavoidably during production is extremely small compared with the amount of glucose or galactose added later as an excipient. For these reasons, the influence of glucose or galactose that is contained unavoidably during production on lactose has not been considered particularly and has been ignored from the viewpoint of the conventional common technical knowledge. Furthermore, when lactase is in a powdery form, i.e., a dried form, there is no influence by water as disclosed in Patent Document 3 or the like and, therefore, there is no incentive to take glucose or galactose contained unavoidably during production into consideration.

However, the present inventors have found that glucose or galactose contained unavoidably during production can greatly affect the storage stability of lactase even if glucose or galactose is contained in a small amount and the influence can reach dried lactase.

An object of the present invention is to provide a lactase bulk powder and a lactase preparation each having further improved storage stability.

The present inventors have found that the stability of a lactase bulk powder can be improved by presetting the acceptable amount of glucose and/or galactose, which is produced unavoidably in the process of the production of lactase, within a specified range. The present inventors have also found that, in the lactase bulk powder having the above-mentioned specified glucose and/or galactose content, even when the lactase bulk powder is mixed in a dried state with an excipient and the resultant mixture is formulated into a lactase preparation, adverse effects of a reducing sugar derived from the excipient on lactase can be suppressed. The present invention has been accomplished on the basis of these findings.

The present invention includes the following inventions.
1. A lactase bulk powder comprising lactase and galactose and/or glucose, wherein a total amount of galactose and glucose is more than 0 μmol and equal to or less than 50 μmol per 100,000 units of lactase.
2. The lactase bulk powder according to item 1, wherein the total amount of galactose and glucose is more than 0 μmol and equal to or less than 30 μmol per 100,000 units of lactase.
3. The lactase bulk powder according to item 1, wherein the total amount of galactose and glucose is more than 0 μmol and equal to or less than 8 μmol per 100,000 units of lactase.
4. The lactase bulk powder according to any one of items 1 to 3, wherein a residual activity after being allowed to leave at 105° C. for 4 hours is 10% or more.
5. The lactase bulk powder according to any one of items 1 to 3, wherein a residual activity after being allowed to leave at 105° C. for 4 hours is 50% or more.
6. The lactase bulk powder according to any one of items 1 to 3, wherein a residual activity after being allowed to leave at 105° C. for 4 hours is 75% or more.
7. The lactase bulk powder according to any one of items 1 to 6, wherein lactase is one produced by *Aspergillus oryzae*.
8. A lactase preparation comprising the lactase bulk powder as recited in any one of items 1 to 7.
9. The lactase preparation according to item 8, wherein a residual activity after being allowed to leave at 105° C. for 4 hours is 10% or more.
10. The lactase preparation according to item 8 or 9, further comprising a sugar excipient.
11. The lactase preparation according to item 10, wherein a content of the sugar excipient is 10% by mass or more.
12. The lactase preparation according to any one of items 8 to 11, wherein a total amount of galactose and glucose in the lactase preparation is more than 0 μmol per 100,000 units of lactase.
13. The lactase preparation according to any one of items 8 to 12, wherein the lactase preparation is a medicine.
14. The lactase preparation according to any one of items 8 to 12, wherein the lactase preparation is a supplement.
15. The lactase preparation according to any one of items 8 to 12, wherein the lactase preparation is a food additive.
16. A method for producing a lactase bulk powder, comprising steps of:
(1) providing a lactase-containing solution which contains glucose and galactose in a total amount of more than 0 μmol and equal to or less than 50 μmol per 100,000 units of lactase; and
(2) drying the lactase-containing solution.
17. A method for producing a lactase preparation, comprising steps of:
(1) providing a lactase-containing solution which contains glucose and galactose in a total amount of more than 0 μmol and equal to or less than 50 μmol per 100,000 units of lactase;
(2) drying the lactase-containing solution; and
(3) formulating a dried lactase product into a preparation.
18. A method for producing a medicine, comprising a step of mixing the lactase bulk powder as recited in any one of items 1 to 7 or the lactase preparation as recited in any one of items 8 to 12 with other component and/or shaping.
19. A method for producing a supplement, comprising a step of mixing the lactase bulk powder as recited in any one of items 1 to 7 or the lactase preparation as recited in any one of items 8 to 12 with other component and/or shaping.
20. A method for producing a food additive, comprising a step of mixing the lactase bulk powder as recited in any one of items 1 to 7 or the lactase preparation as recited in any one of items 8 to 12 with other component and/or shaping.

21. A method for producing a food or beverage, comprising a step of adding the lactase bulk powder as recited in any one of items 1 to 7 or the lactase preparation as recited in any one of items 8 to 12 and 15 to a food or beverage material.

According to the present invention, a lactase bulk powder and a lactase preparation each having further improved storage stability can be provided.

DETAILED DESCRIPTION

Figure 1:
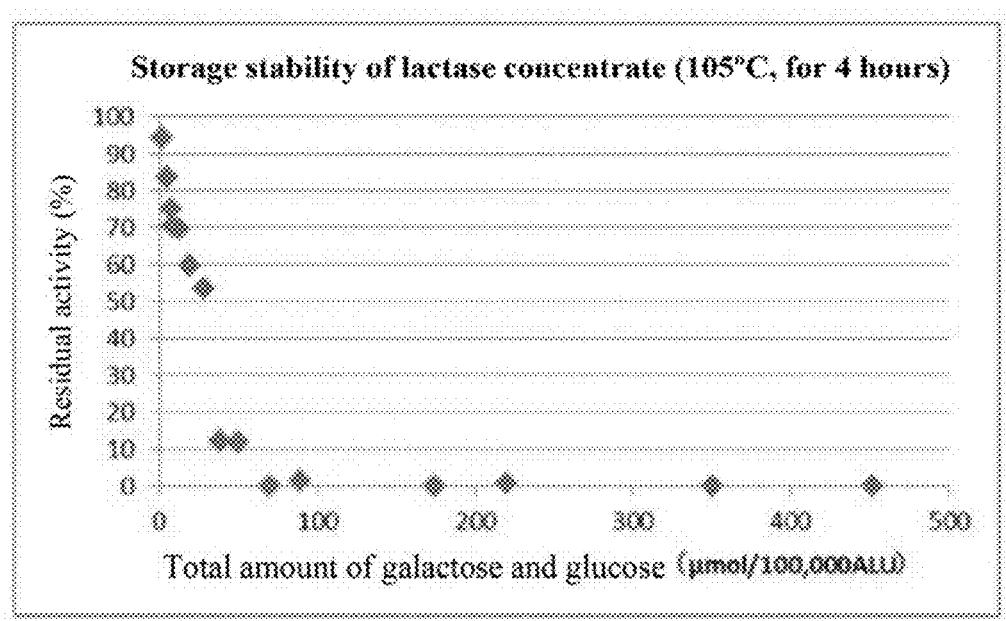
FIG. 1 is a graph produced by plotting the relationship between the total amount of galactose and glucose and a residual activity, which is associated with the storage stability of dried lactase concentrates produced in Examples 1 to 9 and Comparative Examples 1 to 6.

[1. Lactase Bulk Powder (Dried Lactase Concentrate)]

The lactase bulk powder according to the present invention is a lactase concentrate in a dried state, i.e., a lactase bulk powder to which any substance is not added after a drying step that is the final step in the process of the production of the lactase bulk powder, wherein a specified amount of the contamination of glucose and/or galactose is acceptable.

In addition, the lactase bulk powder may also be contaminated by a component produced during the process of the production of the lactase bulk powder (e.g., a component of a culture medium, a protein contaminant produced during a culture process or the like, a component added in the process of the production of the lactase bulk powder). From the viewpoint of industrial production, it is preferred that the component is contained to such an extent that the deterioration in stability cannot be greatly affected. The form of the lactase bulk powder is not particularly limited, and examples of the form include a powdery form and a granular form, preferably a powdery form.

[1-1. Lactase]

The origin of lactase to be contained in the lactase bulk powder is not particularly limited, as long as lactase is produced industrially by utilizing a fermentation activity of a microorganism. A specific example of lactase is lactase isolated from a microorganism such as a fungus, yeast and a bacterium. Among the microorganisms, examples of the fungus include: a fungus belonging the genus *Aspergillus*, such as *Aspergillus oryzae*, *Aspergillus flavus*, *Aspergillus candidus* and *Aspergillus niger*; and a fungus belonging to the genus *Penicillium*, such as *Penicillium multicolor*. Examples of the yeast include: yeast belonging to the genus *Cryptococcus*, such as *Cryptococcus terrestris* and *Cryptococcus laurentii*; yeast belonging to the genus *Sporobolomyces* such as *Sporobolomyces singularis*; yeast belonging to the genus *Kluyveromyces*, such as *Kluyveromyces lactic*; *Saccharomyces fragilis*; *Torula cremoris* and *Torula utilis*. Examples of the bacterium include: *Escherichia coli*; a bacterium belonging to the genus *Bacillus*, such as *Bacillus subtilis*, *Bacillus stearothermophilus*, *Bacillus circulars*, *Bacillus licheniformis* and *Bacillus amyloliquefaciens*; and a lactic acid bacterium including a bacterium belonging to the genus *Lactococcus*, a bacterium belonging to the genus *Lactobacillus* such as *Lactobacillus bulgaricus*, a bacterium belonging to the genus *Streptococcus* and a bacterium belonging to the genus *Bifidobacterium*. The microorganism may be used without any modification as a lactase producer microorganism, or may be used as a host to be used in the production of lactase by the genetic recombination of the lactase gene thereof or a lactase gene originated from a different microorganism. Alternatively, a lactase gene originated from the microorganism may be genetically engineered in a host that is different from the above-mentioned microorganism upon use.

Among the microorganisms, a fungus belonging to the genus *Aspergillus* is preferred, from the viewpoint of achieving the stability improving effect satisfactorily. Among the fungi belonging to the genus *Aspergillus*, *Aspergillus oryzae* is the most preferred. A specific example of *Aspergillus oryzae* is *Aspergillus oryzae* strain RIB40. The microorganism may be a microorganism which is produced by subjecting the above-mentioned microorganism to a mutagenesis treatment by a treatment with ultraviolet ray or the like and then screening by employing the presence of a lactase activity as an indicator so as to have improved lactase productivity, or may be a microorganism which is produced by introducing a lactase gene by genetic engineering so as to have improved lactase productivity.

The amount of lactase to be contained in the lactase bulk powder may be, for example, 1 to 99% by mass inclusive, preferably 10 to 95% by mass inclusive, more preferably 50 to 90% by mass inclusive, still more preferably 75 to 85% by mass inclusive.

The lactase activity of the lactase bulk powder is not particularly limited, and is, for example, 1,000 to 200,000 ALU/g, preferably 2,000 to 150,000 ALU/g, more preferably 5,000 to 150,000 ALU/g, still more preferably 10,000 to 150,000 ALU/g, particularly preferably 50,000 to 150,000 ALU/g. In this regard, "1 ALU (1 Acid Lactase Unit)" refers to an amount of an enzyme required for causing o-nitrophenol release in an amount of 1 μmol per 1 minute when the enzyme is reacted with o-nitrophenyl-β-galactopyranoside (ONPG) that serves as a substrate at a reaction temperature of 37° C., at a reaction pH of 4.5 for 15 minutes.

[1-2. Glucose and Galactose]

In the lactase bulk powder, only glucose may be contained, or only galactose may be contained, or both of glucose and galactose may be contained. It is preferred that only galactose is contained.

Both of glucose and galactose are reducing sugars which are produced unavoidably in the process of the production of the lactase bulk powder, and are not derived from an additive that is not involved in the production of the lactase bulk powder, e.g., a powdery sugar additive such as a carbohydrate excipient to be added to a powdery lactase bulk powder. Specific examples of the reducing sugar that is produced unavoidably in the process of the production of the lactase bulk powder include: a substance derived from a culture medium used in the process of the production of the lactase bulk powder; a substance derived from a sugar metabolized by a microorganism used for the production of the lactase bulk powder; a sugar modified with a protein metabolized by a microorganism used for the production of the lactase bulk powder; and a sugar added before a drying step that is the final step of the process of the production of the lactase bulk powder, or a substance derived from the sugar.

The total amount of glucose and galactose to be contained in the lactase bulk powder is more than 0 μmol, preferably 0.1 μmol or more, more preferably 1 μmol or more, relative to 100,000 units of lactase from the viewpoint of industrial production efficiency, and is 50 μmol or less per 100,000 units of lactase from the viewpoint of the improvement in stability of lactase. From the viewpoint of achieving these effects more satisfactorily, the total amount is, for example, more than 0 μmol and equal to or less than 50 μmol, preferably 0.1 to 50 μmol inclusive, more preferably 1 to 50 μmol inclusive, and is preferably more than 0 μmol and equal to or less than 30 μmol, more preferably 0.1 to 30 μmol inclusive, still more preferably 1 to 30 μmol inclusive, more preferably more than 0 μmol and equal to or less than 9 μmol, further preferably 0.1 to 9 μmol inclusive, still further preferably 1 to 9 μmol inclusive, still further preferably more than 0 μmol and equal to or less than 8 μmol, still more preferably 0.1 to 8 μmol inclusive, still further preferably 1 to 8 μmol inclusive, more further preferably more than 0 μmol and equal to or less than 6 μmol, still more further preferably 0.1 to 6 μmol inclusive, particularly preferably 1 to 6 μmol inclusive, still more preferably more than 0 μmol and equal to or less than 2 μmol, especially preferably 0.1 to 2 μmol inclusive, most preferably 1 to 2 μmol inclusive, per 100,000 units of lactase.

The total amount of glucose and galactose can be adjusted by properly combining, for example, the concentration/desaltation with an ultrafiltration membrane, salting-out such as ammonium sulfate precipitation, dialysis and various types of chromatography using an ion exchange resin and the like. Alternatively, the total amount of glucose and galactose can also be adjusted by using an activity inhibitor for the purpose of avoiding the production of glucose or galactose from a remaining sugar by the action of lactase or a contaminating sugar hydrolase during a process from the completion of culturing to drying, or by appropriately pre-setting conditions under which the reaction cannot proceed easily.

The content proportion of glucose and galactose is not particularly limited. The content of glucose may be higher, or the content of galactose may be higher, or the contents of glucose and galactose may be the same as each other.

[1-3. Other Components]

In the lactase bulk powder, other sugar that is different from the above-mentioned glucose and galactose may be contained. Examples of the "other sugar" include a polysaccharide, an oligosaccharide, a disaccharide, and a monosaccharide other than glucose or galactose. In the case where the "other sugar" is contained, one or more of the above-mentioned sugars may be contained in a mixed state. The content of the "other sugar" to be contained in the lactase bulk powder may be, for example, 0 to 50% by mass inclusive, preferably 0 to 20% by mass inclusive, more preferably 0 to 10% by mass inclusive.

The "other sugar" may be either one of a reducing sugar and a non-reducing sugar. From the viewpoint of achieving good stability of lactase, it is preferred that the amount of the reducing sugar other than glucose or galactose is as small as possible. Examples of the "other reducing sugar" include fructose, maltose and lactose. The total amount of the "other reducing sugars" may be such an amount that the total amount of the reducing sugars (i.e., the sum total of the total amount of glucose and galactose and the total amount of the "other reducing sugars") relative to the whole amount of the lactase bulk powder is, for example, 15 mg or less, preferably 10 mg or less, more preferably 7 mg or less, per 100,000 units of lactase, as measured in terms of a glucose content by a DNS method. In addition, a polysaccharide such as starch, dextrin, indigestible dextrin, trehalose, mannitol, sucrose and sorbitol may be contained. From the viewpoint of achieving good stability of lactase, the total amount of the reducing sugars relative to the whole amount of the lactase bulk powder is preferably an amount falling within the above-mentioned range in which the stability of lactase cannot be affected by the addition of the polysaccharide.

In addition to the above-mentioned components, the lactase bulk powder may also contain an antiseptic agent, such as a parahydroxybenzoate ester, chlorobutanol, benzyl alcohol, and the like.

[1-4. Storage Stability]

The storage stability of the lactase bulk powder is such that, when the lactase bulk powder is stored under a super-acceleration condition of 105° C. for 4 hours, the residual activity becomes, for example, 10% or more, preferably 50% or more, more preferably 70% or more, still more preferably 75% or more, further preferably 80% or more, still further preferably 90% or more, wherein the activity before the storage is 100%.

The storage stability can be controlled by, for example, varying the total amount of glucose and galactose in the lactase bulk powder. When the residual activity is to be set to 10% or more, the total amount may be adjusted to, for example, 50 μmol or less; when the residual activity is to be set to 50% or more, the total amount may be adjusted to, for example, 30 μmol or less; when the residual activity is to be set to 70% or more, the total amount may be adjusted to, for example, 9 μmol or less; when the residual activity is to be set to 75% or more, the total amount may be adjusted to, for example, 8 μmol or less; when the residual activity is to be set to 80% or more, the total amount may be adjusted to, for example, 6 μmol or less; and when the residual activity is to be set to 90% or more, the total amount may be adjusted to, for example, 2 μmol or less.

For the purpose of maintaining the storage stability, it is preferred that the lactase bulk powder is stored under an environment where the temperature and/or humidity is controlled. The storage temperature is room temperature or lower, for example 40° C. or lower, preferably 25° C. or lower. The storage humidity may be such that the relative humidity is for example 80% RH or less, preferably 65% RH or less, at 25° C.

[1-5. Production Method]

The method for producing the lactase bulk powder comprises steps of: providing a lactase-containing solution which contains glucose and galactose in a total amount of more than 0 μmol and equal to or less than 50 μmol per 100,000 units of lactase (step (1)); and drying the lactase-containing solution (step (2)). In each of steps (1) and (2), a procedure that has been employed industrially can be employed without any particular limitation.

An example of the technique for providing the lactase-containing solution in step (1) is a culture method using the above-mentioned microorganism, such as a solid culture method and a liquid culture method, and a liquid culture method can be employed preferably. The culture medium is not particularly limited, as long as a microorganism used can grow therein. For example, a culture medium supplemented with a carbon source such as glucose, sucrose, gentiobiose, soluble starch, glycerin, dextrin, molasses and an organic acid, a nitrogen source such as ammonium sulfate, ammonium carbonate, ammonium phosphate, ammonium acetate, peptone, yeast extract, corn steep liquor, a casein hydrolysate, bran, roasted soybean flour and meat extract, or an inorganic salt such as a potassium salt, a magnesium salt, a sodium salt, a phosphate salt, manganese salt, an iron salt and a zinc salt can be used. In order to accelerate the growth of a transformant to be used, a vitamin, an amino acid or the like may be added to the culture medium. In the case where foaming occurs during the culture, a defoaming agent may be added to the culture medium. The culture is carried out under aerobic conditions at a culture medium pH value that is adjusted to, for example, about 3 to 8, preferably about 4 to 7, and a culture temperature of generally about 20 to 40° C., preferably about 25 to 35° C., for 1 to 10 days, preferably 3 to 7 days. As the culture method, a shaking culture method or an aerobic submerged culture method using a jar fermenter can be employed, for example. After the culture is carried out under the above-mentioned conditions, a desired enzyme is collected from a liquid culture or a microbial cell. In the case where the enzyme is to be collected from a liquid culture, the lactase-containing solution can be obtained by, for example, subjecting a culture supernatant to filtration, a centrifugal treatment or the like to remove insoluble substances and then separating and purifying the solution by a proper combination among the concentration or desaltation with an ultrafiltration membrane, the salting-out such as ammonium sulfate precipitation, dialysis, and various types of chromatography using an ion exchange resin or the like. In the case where the enzyme is to be collected from a microbial cell, the lactase-containing solution can be obtained by pulverizing the microbial cell by a pressure treatment, an ultrasonic treatment or the like, and then carrying out the same procedure as mentioned above. Alternatively, the lactase-containing solution may also be obtained by collecting the microbial cell from the liquid culture medium in advance by filtration or a centrifugation treatment, and then carrying out the above-mentioned sequential process (the pulverization of the microbial cell, the separation and the purification).

The total amount of glucose and galactose to be contained in the lactase-containing solution obtained in step (1) is more than 0 µmol, preferably 0.1 µmol or more, more preferably 0.1 µmol or more, more preferably 1 µmol or more, per 100,000 units of lactase, from the viewpoint of the efficacy of the production of the lactase bulk powder; and is 50 µmol or less per 100,000 units of lactase, from the viewpoint of the improvement in stability of lactase. From the viewpoint of achieving these effects more satisfactorily, the total amount is, for example, more than 0 µmol and equal to or less than 50 µmol, preferably 0.1 to 50 µmol inclusive, more preferably 1 to 50 µmol inclusive, and is preferably more than 0 µmol and equal to or less than 30 µmol, more preferably 0.1 to 30 µmol inclusive, still more preferably 1 to 30 µmol inclusive, more preferably more than 0 µmol and equal to or less than 9 µmol, further preferably 0.1 to 9 µmol inclusive, still further preferably 1 to 9 µmol inclusive, still further preferably more than 0 µmol and equal to or less than 8 µmol, still more preferably 0.1 to 8 µmol inclusive, still further preferably 1 to 8 µmol inclusive, more further preferably more than 0 µmol and equal to or less than 6 µmol, still more further preferably 0.1 to 6 µmol inclusive, particularly preferably 1 to 6 µmol inclusive, still more preferably more than 0 µmol and equal to or less than 2 µmol, especially preferably 0.1 to 2 µmol inclusive, most preferably 1 to 2 µmol inclusive, per 100,000 units of lactase.

In step (2), the lactase-containing solution which is produced in step (1) and contains glucose and galactose in a total amount of more than 0 µmol and equal to or less than 50 µmol per 100,000 units of lactase is dried. Examples of the technique for the drying include freeze drying, vacuum drying and spray drying. In this manner, the lactase bulk powder can be produced. In the method for producing the lactase bulk powder, any step of adding any component is not included subsequent to step (2).

[1-6. Use]

The lactase bulk powder may be used without any modification in a specific use. The lactase bulk powder may also be used as a raw material in the production of a lactase preparation that can be used in a specific use.

Examples of the specific use of the lactase bulk powder include a use as an enzyme drug for industrial purposes and an enzyme reagent.

Examples of the use application as an enzyme drug for industrial purposes include a use as a medicine, a use as a supplement, and a use as a food additive (i.e., a substance intended to be added to a food or a beverage, regardless of professional use or home use), and also include a use for the production of a food or beverage.

An example of the production of a medicine is the production of a medicine which is for a lactase intolerance person and to which the lactase bulk powder of the present invention is added. In the production of the medicine, a step of mixing the lactase bulk powder of the present invention with other component and/or shaping the lactase bulk powder or a mixed product thereof may be included. Examples of the "other component" include an excipient, a preservative agent and a stabilizing agent. Examples of the shaping include powderization, granulation and tableting. Alternatively, in the production of the medicine, a step mentioned below in the section "Production method" of the lactase preparation may be carried out.

An example of the production of a supplement is the production of a dietary supplement (a health food), to which the lactase bulk powder of the present invention is added. In the production of a supplement, a step of mixing the lactase bulk powder of the present invention with other component and/or shaping the lactase bulk powder or a mixed product thereof may be included. Examples of the "other component" include an excipient, a lactic acid bacterium, a vitamin, a mineral and an amino acid. Examples of the shaping include powderization, granulation and tableting. Alternatively, in the production of the supplement, a step mentioned below in the section "Production method" of the lactase preparation may be carried out.

An example of the production of a food additive is the production of an additive to be added to a raw material for the production of a lactose-containing food or beverage (e.g., a dairy product such as milk, yogurt, cheese, butter, cream, powder milk) or galactooligosaccharide. In the production of the food additive, a step of mixing the lactase bulk powder of the present invention with other component and/or shaping the lactase bulk powder or a mixed product thereof can be mentioned. Examples of the "other component" include an enzyme (excluding lactase), a preservative agent, a stabilizing agent, an agent for preparation, a sweetening agent and a seasoning agent. Examples of the shaping include powderization, granulation and tableting. Alternatively, in the production of the food additive, a step mentioned below in the section "Production method" of the lactase preparation may be carried out.

Examples of the production of a food or beverage include the production of a food or beverage (e.g., a dairy product such as milk, yogurt, cheese, butter, cream, powder milk) in which lactose is decomposed and the production of a food or beverage in which galactose is transglycosylated and which is treated with the lactase bulk powder of the present invention. In the production of the food or beverage, a step of adding the lactase bulk powder of the present invention to a lactose-containing food or beverage material is included. When the lactose-containing food or beverage material is subjected to lactase-active conditions to advance the lactose decomposition treatment, the food or beverage can become a lactose-decomposed food or beverage. The lactose-containing food or beverage material to which the lactase bulk powder is to be added may be in a form which is complete as a food or beverage but in which lactose is not decomposed yet or in a form which is a food or beverage material (e.g., a raw material or an intermediate material) but in which lactose is not decomposed yet. Accordingly, the timing of the addition of the lactase bulk powder of the present invention may be after the process of producing the lactose-containing food or beverage or during the process of producing the lactose-containing food or beverage.

An example of the use application as an enzyme reagent is a use application as a reagent for use in a biochemical diagnosis.

In the production of the lactase preparation, a step mentioned below in the section "Production method" of the lactase preparation may be carried out.

[2. Lactase Preparation]

The lactase preparation may be any one, as long as the lactase preparation is formulated with the addition of the lactase bulk powder as an active ingredient. Examples of the lactase preparation include one which is formulated as a shaped product of the lactase bulk powder, one which is formulated as a mixture of the lactase bulk powder with other component, and one which is formulated as a shaped product of a mixture of the lactase bulk powder with other component. Preferably, the lactase preparation is formulated with the addition of other component. The dosage form of the lactase preparation is not particularly limited, as long as the lactase preparation can be ingested orally. Examples of the dosage form include a powder, granules, pills, tablets, capsules and a lozenge.

[2-1. Lactase]

The amount of lactase to be contained in the lactase preparation may be, for example, 1 to 99% by mass inclusive, preferably 10 to 90%% by mass inclusive, more preferably 55 to 65%% by mass inclusive.

[2-2. Sugar Excipient]

The lactase preparation of the present invention may contain a sugar excipient as the "other component". The sugar excipient that may be contained in the lactase preparation of the present invention is not a sugar excipient which is added to a lactase solution to be concentrated during the concentration of lactase, but a sugar excipient which is mixed in a dried state with the lactase bulk powder that is concentrated and is therefore in a dried state.

The sugar excipient is a sugar that can be used as an excipient, and may be in a solid form at room temperature. The sugar excipient may have a galactose residue and/or a glucose residue as a constituent sugar residue. Examples of the sugar excipient include dextrin, indigestible dextrin, starch, potato starch, corn starch, sucrose, mannitol, sorbitol, lactose and trehalose. Because the lactase bulk powder has good storage stability, the amount of the sugar excipient to be added is not particularly limited, as long as the sugar excipient is in a dried state. From the viewpoint of achieving a better shaping effect and/or better storage stability, the amount of the sugar excipient in the lactase preparation can be adjusted appropriately and may be, for example, 10 to 90% by mass inclusive, more preferably 15 to 80% by mass inclusive, still more preferably 20 to 70% by mass inclusive.

[2.3 Glucose and Galactose]

In the case where the lactase preparation of the present invention contains the sugar excipient, the lactase preparation may contain galactose and/or glucose produced from the sugar excipient by the action of lactase. The total amount of galactose and glucose to be contained in the lactase preparation is sum total of the total amount of galactose and glucose produced from the sugar excipient by the action of lactase and the total amount of galactose and glucose contained in the lactase bulk powder, and can be adjusted appropriately from the viewpoint of achieving a good shaping effect and/or good storage stability of the lactase preparation. The total amount may be, for example, more than 0 μmol, preferably 0.1 to 1000 μmol inclusive, more preferably 1 to 500 μmol inclusive, still more preferably 5 to 300 μmol inclusive, still further preferably 50 to 200 μmol inclusive, per 100,000 units of lactase.

[2-4. Storage Stability]

The lactase preparation of the present invention can have good storage stability even when a sugar excipient is contained as the "other component". More specifically, the storage stability of the lactase preparation is such that, when the lactase preparation is stored under super-acceleration conditions of 105° C. for 4 hours, the residual activity becomes, for example, 10% or more, preferably 50% or more, more preferably 70% or more, still more preferably 75% or more, wherein the activity before the storage is 100%.

For the purpose of maintaining the storage stability, it is preferred that the lactase preparation is stored under an environment where the temperature and/or humidity is controlled. The storage temperature is room temperature or lower, for example 40° C. or lower, preferably 25° C. or lower. The storage humidity may be such that the relative humidity is for example 80% RH or less, preferably 65% RH or less, at 25° C.

[2-5. Additional Other Components]

The lactase preparation of the present invention may contain additional other component that is different from the sugar excipient as "other component". Examples of the "additional other component" include an excipient other than the sugar excipient, a lubricant agent, a disintegrating agent, an antiseptic agent and an antacid. An example of the excipient other than the sugar excipient is an inorganic excipient such as talc. Examples of the lubricant agent include aluminum stearate, magnesium stearate, calcium stearate and poly(ethylene glycol). Examples of the disintegrating agent include sodium carboxymethyl starch, carmellose potassium, carmellose and corn starch. Examples of the antiseptic agent include a paraoxybenzoate ester, chlorobutanol and benzyl alcohol. Examples of the antacid include trisodium citrate, potassium sodium tartrate, calcium carbonate, sodium carbonate and dibasic calcium phosphate. In addition to the above-mentioned components, a component (additive) may be selected appropriately by a person skilled in the art depending on the intended use of the lactase preparation (e.g., a medicine, a supplement, a food additive) as the "other component". Examples of the component include a preservative agent, a stabilizing agent, a lactic acid bacterium, a vitamin, a mineral, an amino acid, an agent for preparation, a sweetening agent and a seasoning agent.

[2-6. Production Method]

The lactase preparation can be produced by, for example, formulating the lactase bulk powder into the preparation. The method for producing the lactase preparation comprises the above-mentioned steps (1) and (2) and step (3) of formulating the lactase bulk powder into the preparation. In step (3), the shaping of the lactase bulk powder and/or the mixing of the lactase bulk powder with other component is carried out. Examples of the shaping include powderization, granulation and tableting. The "other component" is as mentioned above. In this manner, a preparation having an arbitrary orally-ingestible dosage form (e.g., a powder, granules, pills, tablets, capsules, and a lozenge) can be prepared. Step (3) is preferably carried out in a dried state from start to finish. In the case where the formulation is carried out using a sugar excipient, both of the lactase bulk powder and the sugar excipient are mixed together in a dried state. A mixture containing the lactase bulk powder and the sugar excipient can be obtained as a lactase preparation without the need to be liquefied.

[2-7. Use]

The lactase preparation may be used without any modification in a specific use application. Examples of the specific use application of the lactase preparation include a use as an enzyme drug for industrial purposes and an enzyme reagent.

Examples of the use application as an enzyme drug for industrial purposes include a use as a medicine, a use as a supplement, and a use as a food additive (i.e., a substance intended to be added to a food or a beverage, regardless of professional use or home use), and also include a use for the production of a food or beverage.

An example of the production of a medicine is the production of a medicine for a lactase intolerance person, to which the lactase preparation of the present invention is added. In the production of the medicine, a step of mixing the lactase preparation of the present invention with other component and/or shaping the lactase preparation or a mixed product thereof may be included. Examples of the "other component" include an excipient, a preservative agent and a stabilizing agent. Examples of the shaping include powderization, granulation and tableting.

An example of the production of a supplement is the production of a dietary supplement (a health food), to which the lactase preparation of the present invention is added. In the production of the supplement, a step of mixing the lactase powder of the present invention with other component and/or shaping the lactase powder of the present invention or a mixed product thereof may be included. Examples of the "other component" include an excipient, a lactic acid bacterium, a vitamin, a mineral and an amino acid. Examples of the shaping include powderization, granulation and tableting.

An example of the production of a food additive is the production of an additive to be added to a raw material for the production of a lactose-containing food or beverage (e.g., a dairy product such as milk, yogurt, cheese, butter, cream, powder milk) or galactooligosaccharide. In the production of the food additive, a step of mixing the lactase powder of the present invention with other component and/or shaping the lactase powder or a mixed product thereof can be mentioned. Examples of the "other component" include an enzyme (excluding lactase), a preservative agent, a stabilizing agent, an agent for preparation, a sweetening agent and a seasoning agent. Examples of the shaping include powderization, granulation and tableting.

Examples of the production of a food or beverage include the production of a food or beverage (e.g., a dairy product such as milk, yogurt, cheese, butter, cream, powder milk) in which lactose is decomposed and the production of a food or beverage in which galactose is transglycosylated and which is treated with the lactase preparation of the present invention. In the production of the food or beverage, a step of adding the lactase preparation of the present invention to a lactose-containing food or beverage material is included. When the lactose-containing food or beverage material is appropriately subjected to lactase-active conditions to advance the lactose decomposition treatment, the food or beverage can become a lactose-decomposed food or beverage. The lactose-containing food or beverage material to which the lactase preparation is to be added may be in a form which is complete as a food or beverage but in which lactose is not decomposed yet or in a form which is a material (e.g., a raw material or an intermediate material) for a food or beverage but in which lactose is not decomposed yet. Accordingly, the timing of the addition of the lactase preparation of the present invention may be after the production of the lactose-containing food or beverage or during the process of producing the lactose-containing food or beverage.

An example of the use application as an enzyme reagent is a use application as a reagent for use in a biochemical diagnosis.

EXAMPLES

Example 1

(A) Preparation of Lactase Bulk Powder (Dried Lactase Concentrate)

A lactase bulk powder (dried lactase concentrate) was prepared in the following manner.

1. A producer fungus (*Aspergillus oryzae*) was cultured by liquid culture at 30° C. for 5 days. A culture medium supplemented with 4 w/v % of wheat bran, 1 w/v % of roasted soybean flour, 0.25 w/v % of ammonium phosphate and 3 w/v % of soluble starch was used.
2. Cells of the producer fungus were removed by the filtration through diatomaceous earth.
3. The liquid was concentrated with an ultrafiltration membrane until the activity of the lactase bulk powder became 10,000 ALU/g or more.
4. A step of adding an equal volume of water and subsequently concentrating to the original liquid volume using an ultrafiltration membrane was repeated five times or more to perform desaltation, and total amount of galactose and glucose was adjusted.
5. The resultant solution was powderized by spray drying or freeze drying.

(B) Measurement of Galactose Content and Glucose Content

The galactose content in the dried lactase concentrate was measured using a galactose measurement kit Lactose/D-Galactose (R-Biopharm, catalog No. 10 176 303 035) on an automatic analysis device TBA-120FR (Toshiba Medical Systems Corporation).

The glucose content in the dried lactase concentrate was measured using a glucose measurement kit Glucose CII-Test Wako (Wako Pure Chemical Industries, Ltd., Code 439-90901).

(C) Measurement of Total Amount of Reducing Sugars

The total amount of reducing sugars in the dried lactase concentrate was measured by employing DNS method (dinitrosalicylic acid method). More specifically, 0.6 mL of a DNS solution ((0.7 w/v % of 3,5-dinitrosalicylic acid, 1.21 w/v % of sodium hydroxide, 0.02 w/v % of sodium potassium tartrate, 0.57 w/v % of phenol, 0.55 w/v % of sodium hydrogen carbonate) was dispensed in a test tube, and then 0.2 mL of a lactase solution prepared by diluting the dried lactase concentrate with purified water to a proper concentration was added thereto. The resultant solution was thermally color-developed in boiled water for 5 minutes, was then cooled for 15 minutes in flowing water and was then added with 4.2 mL of purified water, and then the absorbance of the resultant solution at 550 nm was measured with a spectrophotometer. Separately, the same procedure was carried out, except that glucose solutions (0, 0.5, 1, 2, 3, 4, 5 mg/mL) were used in place of the lactase solution to produce a glucose calibration curve. The total amount of reducing sugars in the dried lactase concentrate was calculated in terms of glucose content from the calibration curve.

(D) Storage Stability

The storage stability of the dried lactase concentrate was evaluated by an accelerated storage stability test. The acceleration condition was such that the dried lactase concentrate was stored at 105° C. for 4 hours. In the evaluation, a residual activity (%) was calculated from lactase activities before and after the storage under the acceleration condition in accordance with the following equation.

Residual activity (%)=(activity (ALU/g) after storage)/(activity (ALU/g) before storage)×100

The lactase activity was measured in accordance with the method mentioned as "Lactase (Acid) (β-galactosidase)" in Food Chemical Codex (FCC) standards, fourth edition. More specifically, the amount of an enzyme required for causing o-nitrophenol release in an amount of 1 μmol per 1 minute when the enzyme was reacted with o-nitrophenyl-β-galactopyranoside (ONPG) that served as a substrate at a reaction temperature of 37° C., at a reaction pH of 4.5 for 15 minutes was defined as 1 unit (1 ALU; 1 Acid Lactase Unit)).

Examples 2 to 5, Comparative Examples 1 to 3

The lactase bulk powder (dried lactase concentrate) produced in Example 1 was dissolved in purified water to prepare a lactase solution. Galactose was added to and dissolved in the lactase solution at various concentrations, and then each of the resultant solutions was powderized by freeze drying. In this manner, dried lactase concentrates having different galactose amounts were prepared. With respect to each of the dried lactase concentrates thus produced, the contents of galactose and glucose and the total amount of reducing sugars were measured and the storage stability was evaluated in the same manner as in Example 1.

Examples 6 to 9, Comparative Examples 4 to 6

The lactase bulk powder (dried lactase concentrate) produced in Example 1 was dissolved in purified water to prepare a lactase solution. Glucose was added to and dissolved in the lactase solution at various concentrations, and then each of the resultant solutions was powderized by freeze drying. In this manner, dried lactase concentrates having different galactose amounts were prepared. With respect to each of the dried lactase concentrates thus produced, the contents of galactose and glucose and the total amount of reducing sugars were measured and the storage stability was evaluated in the same manner as in Example 1.

[Results]

The results of Examples 1 to 9 and Comparative Examples 1 to 6 are shown in Table 1. With respect to the storage stability, a graph in which the relationship between the total amount of galactose and glucose and the residual activities was plotted is shown in FIG. 1. A graph produced by enlarging, in the transverse axis direction, a zone in FIG. 1 in which the total amount of galactose and glucose is 50 μmol/100,000 units is shown in FIG. 2.

TABLE 1

|  | Reducing sugar added | Content of galactose (Gal) (1) μmol/100,000 ALU | Content of glucose (Glu) (2) μmol/100,000 ALU | Total content of Gal + Glu ((1) + (2)) μmol/100,000 ALU | Content of reducing sugar (DNS method) mg/100,000 ALU | Storage stability (%) (Residual activity after 4 hours at 105° C.) |
|---|---|---|---|---|---|---|
| Example 1 | (not added) | 1.9 | 0.0 | 1.9 | 4.2 | 94.5 |
| Example 2 | Galactose | 7.9 | 0.0 | 7.9 | 5.3 | 75.0 |
| Example 3 |  | 12.7 | 0.0 | 12.7 | 5.8 | 69.9 |
| Example 4 |  | 28.2 | 0.1 | 28.3 | 7.8 | 53.8 |
| Example 5 |  | 49.3 | 0.4 | 49.7 | 12.0 | 11.9 |
| Comparative Example 1 |  | 87.8 | 1.6 | 89.4 | 17.5 | 1.6 |
| Comparative Example 2 |  | 214.8 | 4.8 | 219.6 | 37.0 | 0.9 |
| Comparative Example 3 |  | 442.4 | 9.9 | 452.3 | 70.4 | 0.0 |
| Example 6 | Glucose | 1.9 | 3.6 | 5.5 | 5.3 | 83.6 |
| Example 7 |  | 1.9 | 6.4 | 8.3 | 5.9 | 70.5 |
| Example 8 |  | 2.0 | 17.3 | 19.3 | 8.5 | 59.7 |
| Example 9 |  | 2.2 | 36.2 | 38.4 | 11.1 | 12.3 |
| Comparative Example 4 |  | 1.9 | 68.0 | 69.9 | 17.0 | 0.1 |
| Comparative Example 5 |  | 1.8 | 172.5 | 174.3 | 36.9 | 0.0 |
| Comparative Example 6 |  | 1.5 | 348.7 | 350.2 | 67.3 | 0.0 |

Figure 2:
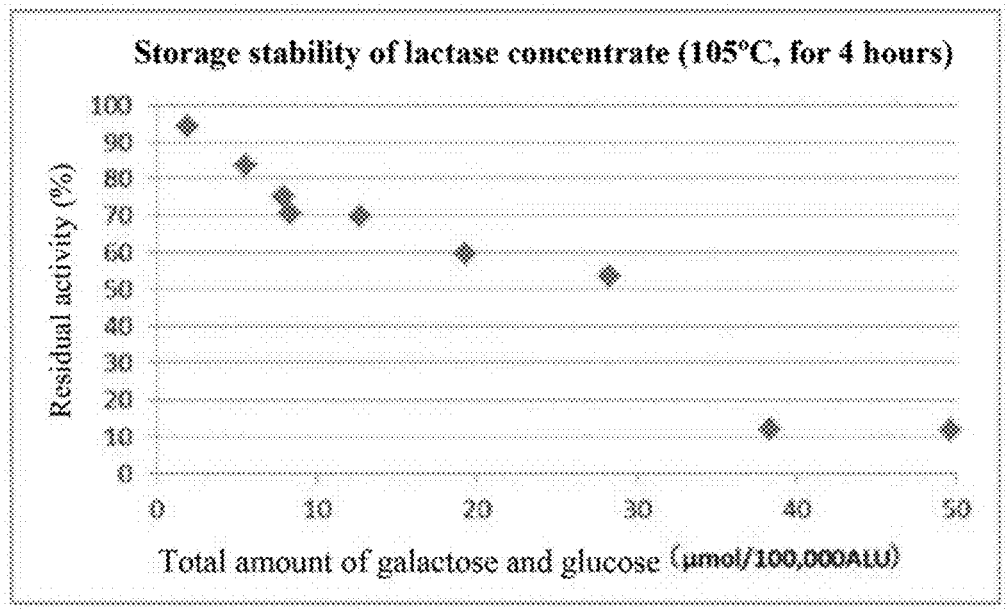
FIG. 2 is a graph produced by enlarging, in the transverse direction, a zone in FIG. 1 in which the total amount of galactose and glucose is 50 μml/100,000 units.

As shown in Table 1 and FIGS. 1 and 2, in Examples 1 to 9 in each of which the total amount of galactose and glucose contained in the lactase solution to be concentrated was 50 μmol/100,000 units or less in terms of a dried content, the improvement in residual activity was observed compared with Comparative Examples 1 to 6 in each of which the total amount was more than 50 μmol/100,000 units or less in terms of a dried content. The residual activity improvement effect was observed more satisfactorily in Examples 1 to 4 and 6 to 8 in each of which the total amount was 30 μmol/100,000 units or less, and was observed still more satisfactorily in Examples 1 to 2 and 6 in each of which the total amount was 8 μmol/100,000 units or less.

Example 10

A lactase bulk powder was prepared in the same manner as in Example 1, and the lactase bulk powder was measured with respect to the contents of galactose and glucose therein and the total amount of reducing sugars therein and was evaluated with respect to the storage stability thereof. The lactase bulk powder contained a protein in an amount of 80±5% by mass and contained a polysaccharide and an oligosaccharide in a total amount of 5±10% by mass.

Example 11

The lactase bulk powder produced in Example 10 was mixed with dextrin that served as an excipient in a dried state to produce a lactase composition. In this manner, a lactase preparation (shaped product) was prepared. The content of dextrin in the resultant shaped product was 20% by mass. The shaped product was measured with respect to the contents of galactose and glucose therein and the total amount of reducing sugars therein and was evaluated with respect to the storage stability thereof in the same manner as in Example 1. The lactase preparation contained a protein in an amount of 60±5% by mass and contained a polysaccharide and an oligosaccharide in a total amount of 25±5% by mass.

[Results]

Figure 3:
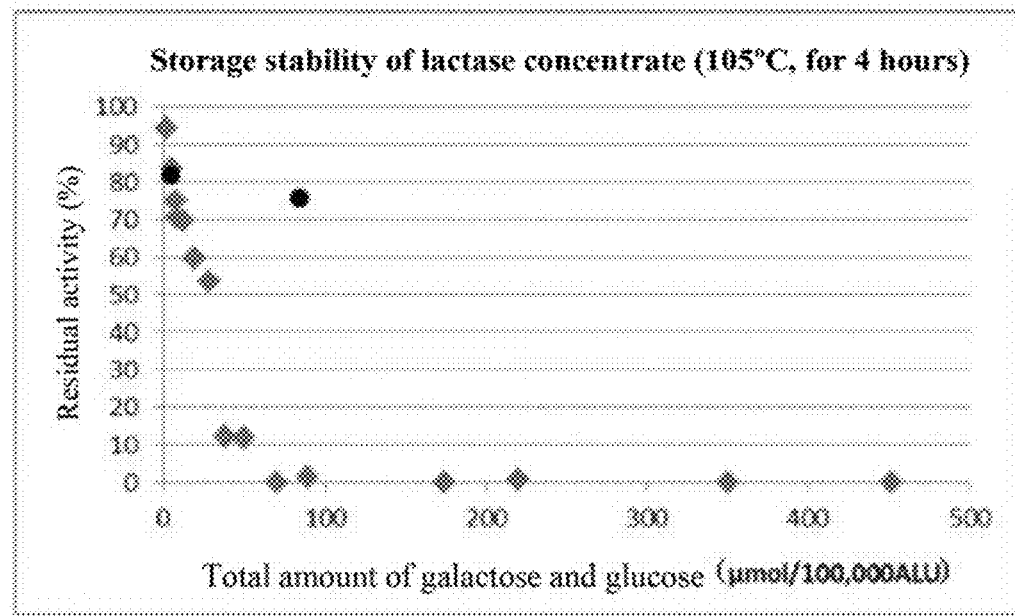
FIG. 3 is a graph produced by plotting the results of a dried lactase concentrate produced in Example 10 and a lactase shaped product produced in Example 11 as circular dots on the graph of FIG. 1.

The results of Examples 10 to 11 are shown in Table 2. In Table 2, the results of Comparative Examples 1 and 4 are also shown for the purpose of comparison. A graph in which the results of Examples 10 to 11 are plotted with circular dots on the graph of FIG. 1 is shown in FIG. 3.

TABLE 2

|  | Content of galactose (Gal) (1) μmol/100,000 ALU | Content of glucose (Glu) (2) μmol/100,000 ALU | Total content of Gal + Glu ((1) + (2)) μmol/100,000 ALU | Content of reducing sugar (DNS method) mg/100,000 ALU | Storage stability (%) (Residual activity after 4 hours at 105° C.) |
|---|---|---|---|---|---|
| Example 10 (Lactase bulk powder) | 4.4 | 0.0 | 4.4 | 5.6 | 82.0 |
| Example 11 (Shaped product) | 4.4 | 79.7 | 84.1 | 30.6 | 76.0 |
| (Comparative Example 1) | 87.8 | 1.6 | 89.4 | 17.5 | 1.6 |
| (Comparative Example 4) | 1.9 | 68.0 | 69.9 | 17.0 | 0.1 |

It was demonstrated that, in the lactase preparation (shaped product) of Example 11, which was prepared by mixing the lactase bulk powder of Example 10 with the excipient in a dried state, the residual activity was maintained at a good level although the total amount of galactose and glucose was increased due to the contamination with reducing sugars derived from the excipient. The total amount of galactose and glucose contained in the lactase preparation (shaped product) of Example 11 was almost the same as that in Comparative Example 1 and was slightly increased than that in Comparative Example 4. However, it was demonstrated that the residual activity in Example 11 was greatly improved compared with those in Comparative Examples 1 and 4 in each of which galactose and glucose were contained in a significant total amount from a time point at which the preparation was not concentrated yet and was in a liquid state onward. Namely, it was demonstrated that, when the total amount of galactose and glucose was adjusted to a reduced amount at a time point at which the preparation was not concentrated yet and was in a liquid state, a sugar excipient did not undesirably affect an enzyme even when the sugar excipient was added after the drying of the preparation.

The preferred embodiments of the present invention are as mentioned above. However, the present invention is not intended to be limited to these embodiments, and various other embodiments may be made without departing from the spirit of the invention.

What is claimed is:

1. A lactase bulk powder comprising lactase and galactose and/or glucose, wherein a total amount of the galactose and the glucose is more than 0 μmol and equal to or less than 30 μmol per 100,000 units of lactase.

2. The lactase bulk powder according to claim 1, wherein the total amount of the galactose and the glucose is more than 0 μmol and equal to or less than 8 μmol per 100,000 units of lactase.

3. The lactase bulk powder according to claim 1, wherein an enzymatic activity after being stored at 105° C. for 4 hours is 50% or more, compared to an enzymatic activity before being stored.

4. The lactase bulk powder according to claim 1, wherein an enzymatic activity after being stored at 105° C. for 4 hours is 75% or more, compared to an enzymatic activity before being stored.

5. The lactase bulk powder according to claim 1, wherein the lactase is produced by *Aspergillus oryzae*.

6. A lactase preparation comprising the lactase bulk powder according to claim 1 and a sugar excipient.

7. The lactase preparation according to claim 6, wherein an enzymatic activity after being stored at 105° C. for 4 hours is 50% or more, compared to an enzymatic activity before being stored.

8. The lactase preparation according to claim 6, wherein a content of the sugar excipient is 10% by mass or more and 90% by mass or less.

9. A method for producing the lactase bulk powder according to claim 1, comprising:
providing a lactase-containing solution which contains glucose and galactose in a total amount of more than 0 μmol and equal to or less than 30 μmol per 100,000 units of lactase; and
drying the lactase-containing solution.

10. A method for producing the lactase preparation according to claim 6, comprising:
providing a lactase-containing solution which contains glucose and galactose in a total amount of more than 0 μmol and equal to or less than 30 μmol per 100,000 units of lactase;
drying the lactase-containing solution; and
formulating a dried lactase product into a preparation.

* * * * *